US011382641B2

United States Patent
Papenfuss

(10) Patent No.: US 11,382,641 B2
(45) Date of Patent: Jul. 12, 2022

(54) REAMING INSTRUMENT WITH OFFSET DRIVE SHAFT

(71) Applicant: Lenkbar, LLC, Naples, FL (US)

(72) Inventor: Erik H. Papenfuss, Naples, FL (US)

(73) Assignee: Lenkbar, LLC, Naples, FL (US)

( * ) Notice: Subject to any disclaimer, the term of this patent is extended or adjusted under 35 U.S.C. 154(b) by 401 days.

(21) Appl. No.: 16/400,366

(22) Filed: May 1, 2019

(65) Prior Publication Data

US 2019/0357924 A1 Nov. 28, 2019

Related U.S. Application Data

(60) Provisional application No. 62/674,861, filed on May 22, 2018.

(51) Int. Cl.
*A61B 17/16* (2006.01)

(52) U.S. Cl.
CPC ...... *A61B 17/1684* (2013.01); *A61B 17/1631* (2013.01); *A61B 17/1615* (2013.01)

(58) Field of Classification Search
CPC ............ A61B 17/1615; A61B 17/1631; A61B 17/1633; A61B 17/1662; A61B 17/1666; A61B 17/1668; A61B 17/1684
See application file for complete search history.

(56) References Cited

U.S. PATENT DOCUMENTS

| | | | |
|---|---|---|---|
| 2004/0073224 A1* | 4/2004 | Bauer | A61B 17/1666 606/81 |
| 2007/0093840 A1* | 4/2007 | Pacelli | A61B 17/1631 606/80 |
| 2015/0119891 A1* | 4/2015 | Goldberg | A61B 17/1631 606/80 |

* cited by examiner

*Primary Examiner* — Anu Ramana
(74) *Attorney, Agent, or Firm* — RatnerPrestia

(57) ABSTRACT

A reaming instrument includes a reamer head having a cutting face rotatable about a cutting face axis and a drive shaft operably connected to the cutting face at a point spaced radially outwardly from the cutting face axis.

26 Claims, 4 Drawing Sheets

REAMING INSTRUMENT WITH OFFSET DRIVE SHAFT

RELATED APPLICATION

This application is related to and claims the benefit of priority under 35 U.S.C. 119 of U.S. Provisional Application Ser. No. 62/674,861, filed May 22, 2018, content of which is incorporated by reference herein in its entirety.

FIELD

The present invention relates generally to minimally invasive surgical instrumentation, and more particularly to a minimally invasive reaming instrument with an offset drive shaft that provides improved access to reaming or drilling sites.

BACKGROUND

Joint arthroplasty procedures, sometimes referred to as "joint replacements", are commonly performed to relieve pain, restore mobility or address other issues caused by injury or degenerative conditions in a joint. Many types of arthroplasty procedures involve a partial or total replacement of the joint with prosthetic implants. In a total joint arthroplasty, the ends of the bones that are adjacent the joint to be replaced are cut away, or partially removed, to prepare and reshape the bone surface so that a prosthetic implant can be securely attached to the bone surface. This process of removing or reshaping the bone is often done with a tool referred to as a reaming instrument or "reamer".

Certain joints, such as the glenohumeral joint (i.e. "shoulder joint"), are surrounded by bones and tissue, making it difficult to access the joint in a minimally invasive procedure. To access these joints with a reamer, the surgeon may have little choice but to make a large incision that accommodates the full profile size of the reamer. Large incisions can traumatize tissue, increase the risk of complications, and take a long time to fully heal.

SUMMARY

Reamers in accordance with this disclosure feature components that facilitate greater maneuverability and minimally invasive access to bone areas and joints.

In a first beneficial aspect of the disclosure, a reaming instrument includes a reamer head having a cutting face, the cutting face rotatable about a cutting face axis.

In another beneficial aspect of the disclosure, a drive shaft is operably connected to the cutting face at a point spaced radially outwardly from the cutting face axis.

In another beneficial aspect of the disclosure, the drive shaft is a flexible drive shaft.

In another beneficial aspect of the disclosure, the drive shaft extends through a sleeve.

In another beneficial aspect of the disclosure, the instrument includes a post.

In another beneficial aspect of the disclosure, the instrument includes a handle portion.

In another beneficial aspect of the disclosure, the reamer head includes a gear box.

In another beneficial aspect of the disclosure, the gear box includes a driver gear and a follower gear.

In another beneficial aspect of the disclosure, the driver gear operatively coupled to the drive shaft.

In another beneficial aspect of the disclosure, the follower gear is operatively coupled to the cutting face.

In another beneficial aspect of the disclosure, the follower gear is connected to an output shaft.

In another beneficial aspect of the disclosure, the output shaft is connected to the cutting face.

In another beneficial-aspect of the disclosure, the output shaft includes a drill bit.

In another beneficial aspect of the disclosure, the reamer head includes a back plate.

In another beneficial aspect of the disclosure, the drive shaft extends through a sleeve attached to the back plate.

In another beneficial aspect of the disclosure, the sleeve and drive shaft attach to the back plate at a right angle.

In another beneficial aspect of the disclosure, the sleeve defines a sleeve that extends parallel to but offset from the cutting face axis.

In another beneficial aspect of the disclosure, the back plate includes a first plate section having a first center and a first perimeter that conforms to a first circle extending around the first center.

In another beneficial aspect of the disclosure, the back plate includes a second plate section in the form of a lobe that extends radially outwardly with respect to the first center of the first plate section.

In another beneficial aspect of the disclosure, the lobe defines a second perimeter conforming to a second circle that intersects the first circle.

In another beneficial aspect of the disclosure, the second circle extends around a second center, and the back plate defines an aperture that extends through the second center.

In another beneficial aspect of the disclosure, the drive shaft operably connects to the cutting face through the aperture.

BRIEF DESCRIPTION OF THE DRAWINGS

The detailed description section will be better appreciated when reviewed in conjunction with the drawing figures. The following drawing figures illustrate art exemplary and non-limiting embodiment, and depict elements which can be combined and arranged either as shown, or in other combinations and arrangements.

DETAILED DESCRIPTION

Figure 1:
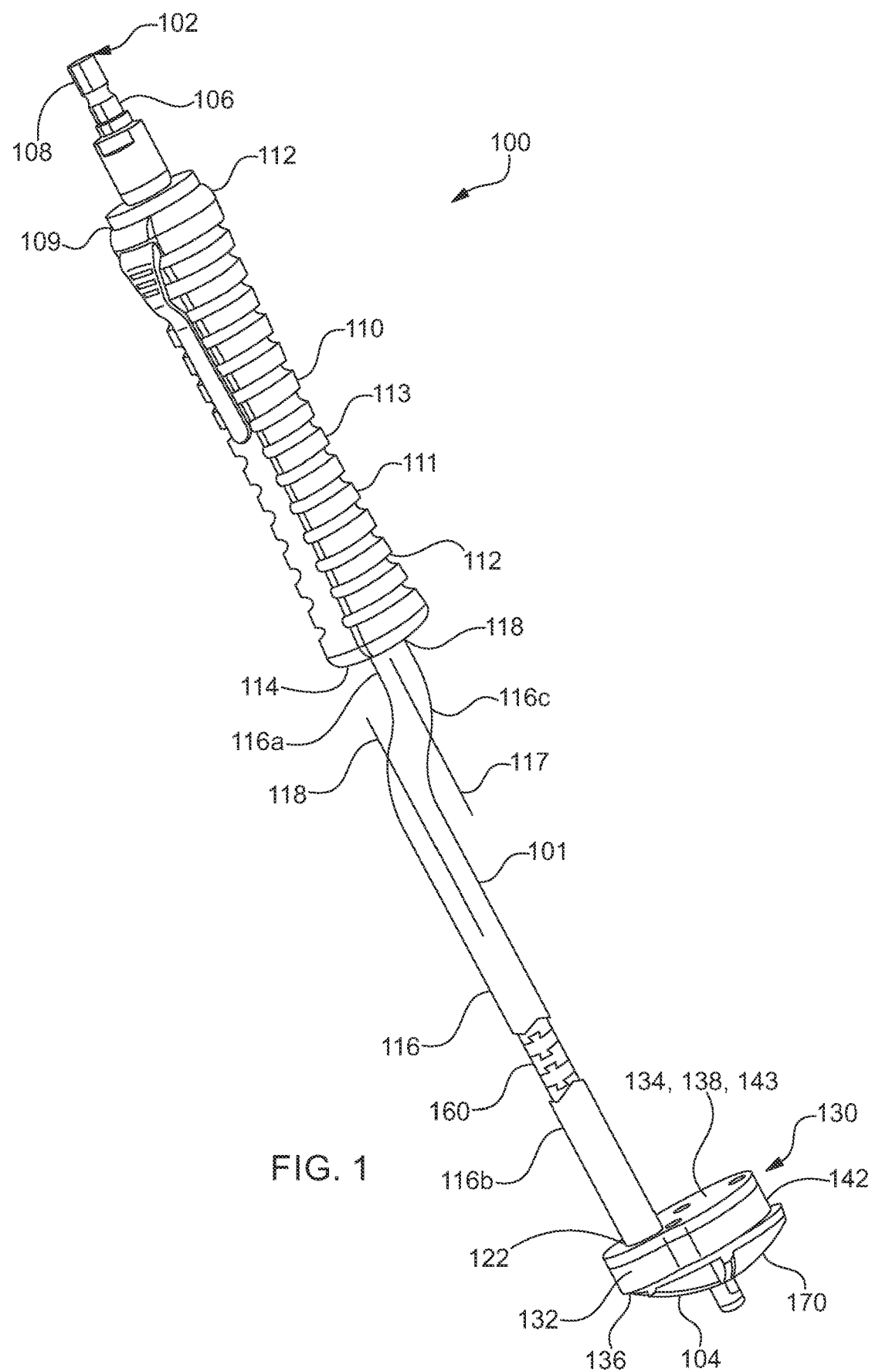
FIG. 1 is a perspective view of a reamer in accordance with one embodiment.

Although this disclosure describes specific embodiments, this disclosure is not intended to be limited to the details shown. Various modifications may be made to any of the details described herein, with such modifications falling within the scope of this disclosure and range of equivalents.

Applicants have developed reamers in accordance with this disclosure that provide improved access to bone and joint areas. In one embodiment, a reamer has a rotatable drive shaft having a longitudinal axis or "drive shaft axis". The reamer also has a reamer head with a rotatable cutting face. The drive shaft is operable to rotate the cutting face in response to torque applied to the drive shaft. The cutting face is operable to rotate about a "cutting face axis" in order to shave or cut bone when the cutting face is placed in contact with bone.

Drive shafts and reamer heads in accordance with this disclosure can have a variety of physical arrangements and dimensions that allow the reamer to be inserted and navigated through the body in a minimally invasive manner. In addition, drive shafts and reamer heads in accordance with this disclosure can have a variety of physical arrangements and dimensions that allow the instrument to move around bone and tissue structures to access hard to reach locations. For example, the drive shaft can be connected to the reamer head at a peripheral location of the reamer head, at a location offset from the center of the reamer head. In addition, the cross-sectional area or profile of the drive shaft can be significantly smaller than the cross-sectional area or profile of the reamer head. Moreover, the profile of the drive shaft can be enclosed within the profile of the reamer head toward the outer perimeter of the reamer head. In this arrangement, the profile of the drive shaft occupies a very small portion of the reamer head's profile, and is positioned to one side of the reamer head. Therefore, a substantial portion of the reamer head can be inserted round or behind obstacles without obstruction caused by the drive shaft.

The offset arrangement and relatively small profile of the drive shaft allows the reamer head to be navigated and positioned more easily in confined areas that are hard to access with conventional instrumentation. For example, the offset can allow the reamer head to ream underneath the humeral bone and have better access to the glenoid. The offset also allows the reamer head to slide under other bones and obstructions.

Embodiments described in this section can be used in a shoulder arthroplasty in humans, and more specifically in the preparation of bone surfaces on the glenoid portion of the scapula and the humerus. Embodiments in accordance with this description can also be used on other joints, and are not limited to shoulder arthroplasty procedures. For example, embodiments in accordance with this description can be used for preparing bone surfaces in joints in human wrists, fingers, hips, knees, ankles, toes and the spine. Moreover, embodiments in accordance with this description can be used for boring, reaming or planing bone surfaces, or other procedures for preparing bone surfaces.

Figure 2:
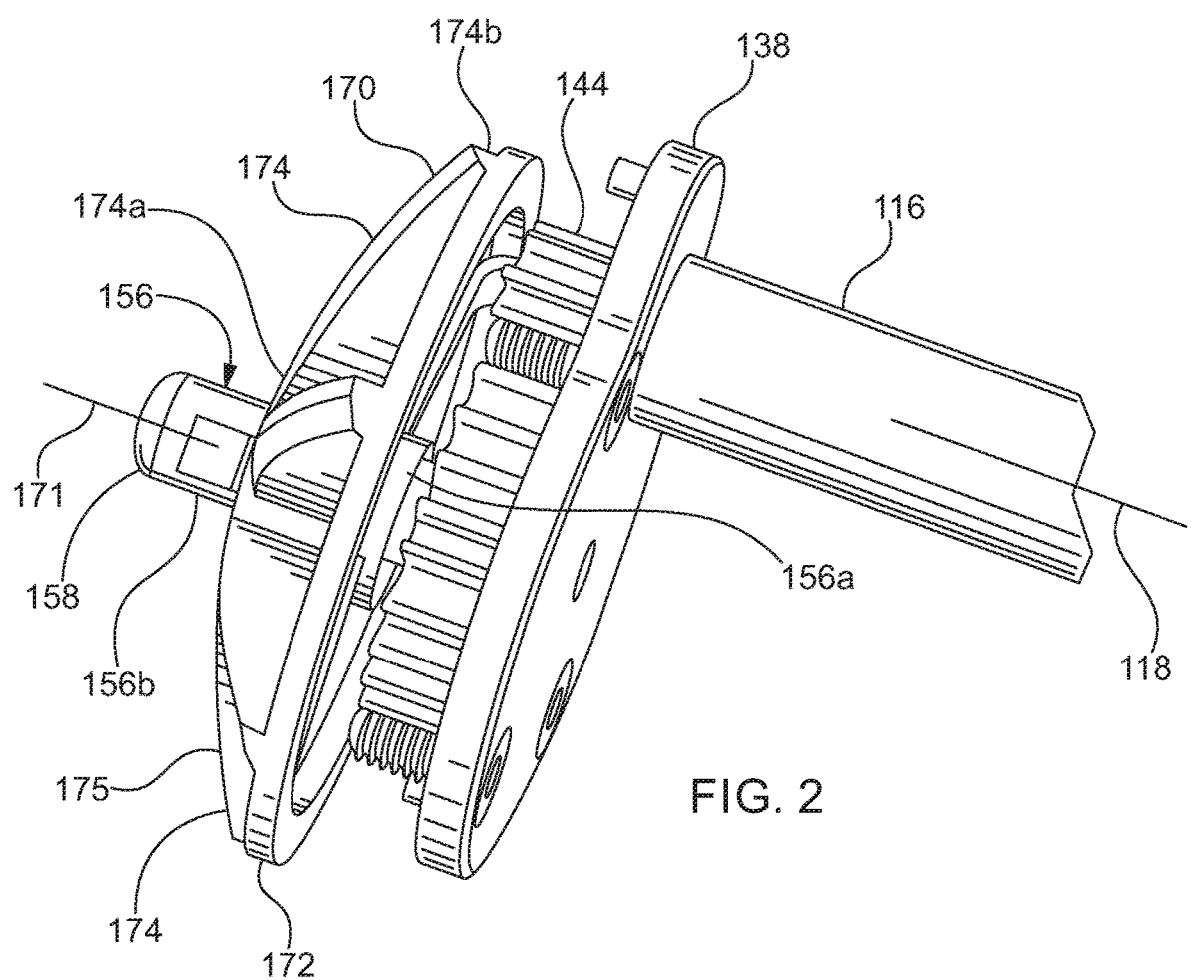
FIG. 2 is a truncated perspective view of a distal end portion of the reamer of FIG. 1, with some components removed for clarity.

Referring now to FIGS. 1 and 2, a reamer 100 is shown in accordance with one possible embodiment. Reamer 100 includes an elongated body 101 having a proximal end 102 and a distal end 104. The term "proximal" is used herein to refer to an instrument end or direction that would be oriented toward the surgeon when the surgical instrument engages a bone during a reaming procedure. The term "distal" is used herein to refer to an instrument end or direction that would be oriented toward the patient being treated when the surgical instrument engages a bone during a reaming procedure.

Proximal end 102 includes a post 106. Post 106 has an engagement end 108 configured to be coupled to a torque driver or drill. Engagement end 108 may have any conventional configuration, such as a hexagonal geometry, to be coupled to a torque driver or drill. Post 106 also has a distal end 109 that connects to a proximal end 112 of a hollow handle section 110. Handle section 110 has an hourglass shape adapted for gripping with one hand. Handle section 110 also has two opposing sides 111, each side having a series of slots 112 that define ridges 113. Slots 112 and ridges 113 are configured to stabilize a user's grip and reduce slippage.

A distal end 114 of handle section 110 is connected to a proximal end 118 of a hollow sleeve 116. Sleeve 116 has first sleeve section 116a having a first sleeve axis 117 that is coaxial with post 106. Sleeve 116 also has a second sleeve section 116b having a second sleeve axis 118 that is parallel to, but offset from, first sleeve axis 117 and post 106. First sleeve section 116a and second sleeve section 116b are joined together by an "S"-curved section 116c.

Second sleeve axis 118 is shown extending perpendicular to a reamer head 130, the features of which will be explained. As will be explained, second sleeve sections according to this disclosure need not be perpendicular to a reamer head, but can approach and intersect the reamer head at various non-perpendicular angles to allow the surgeon to maneuver the instrument around a particular bone or tissue obstruction and/or access a specific joint. Any angulation can be chosen to allow the surgeon to slide the instrument under or over an obstruction, or to fit the instrument into or around bone or tissue. The second sleeve section and its axis also do not need to be parallel to the post or the cutting face axis.

A flexible drive shaft 160 is connected to post 106 and extends through handle section 110 and sleeve 106. A variety of flexible drive shafts can be used within the scope of this disclosure, including but not limited to flexible surgical shafts marketed under the registered trademark FLEXMETRIC® manufactured by Lenkbar, LLC of Naples, Fla. USA, and flexible drive shafts described in U.S. Pat. No. 8,366,559, the content of which is incorporated by reference herein in its entirety. Flexible drive shaft 160 includes at least one flexible portion that allows the flexible drive shaft to pass through "S"-curved section 116c and extend through first and second sleeve sections 116a and 115b.

A distal end 122 of sleeve 116 is connected to a reamer head 130. Reamer head 130 has a gear box 132 having a proximal end 134 and a distal end 136, Proximal end 134 of gear box 132 is connected to distal end 122 of sleeve 115. Distal end 136 of gear box 132 is connected to a cutting face 170, Gear box 132 has a back plate 138 and a sidewall 142. Back plate 138 and sidewall 142 partially enclose a driver gear 144 and a follower gear 146.

Figure 3:
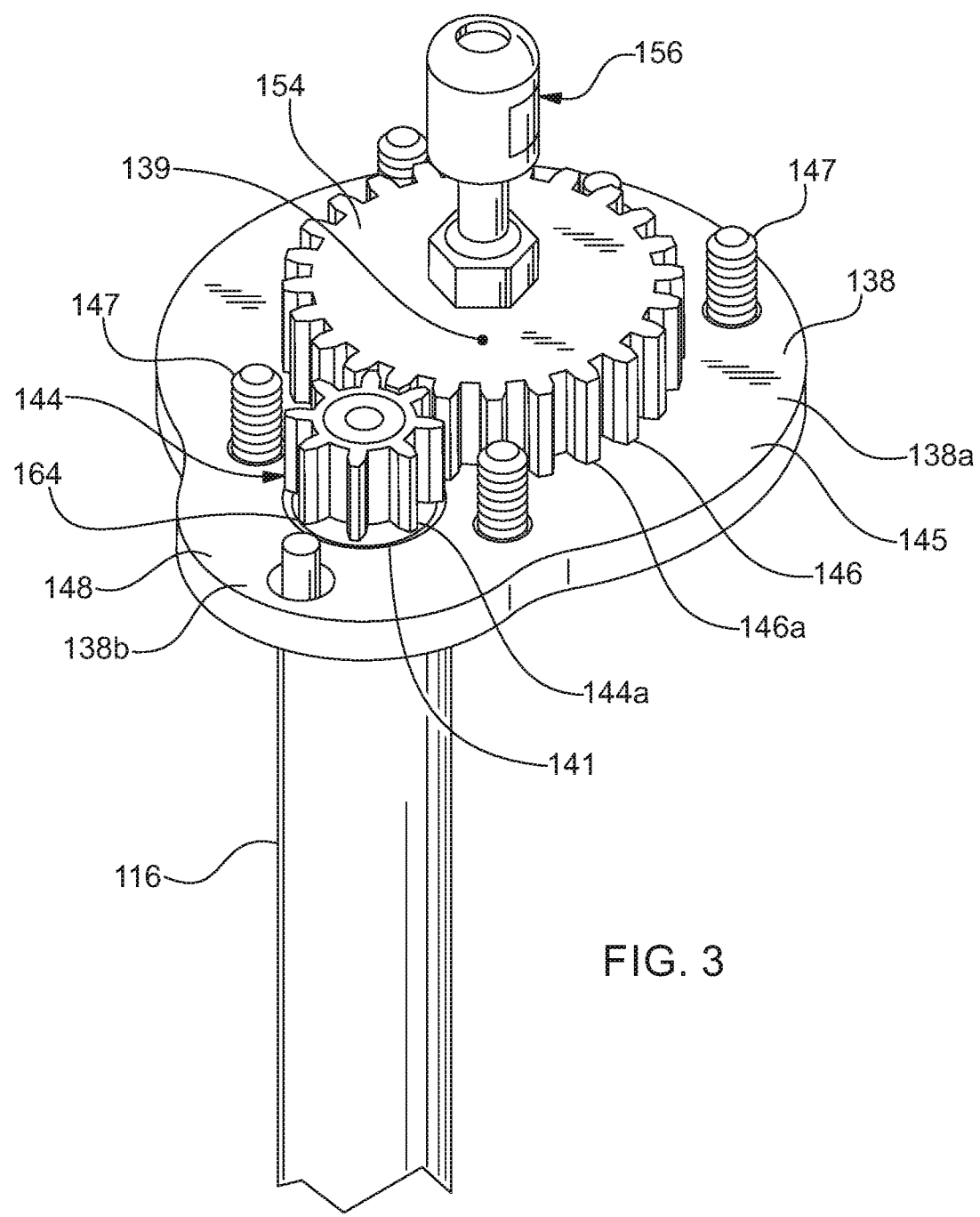
FIG. 3 is another truncated perspective view of a distal end portion of the reamer of FIG. 1, with some components removed for clarity.
Figure 4:
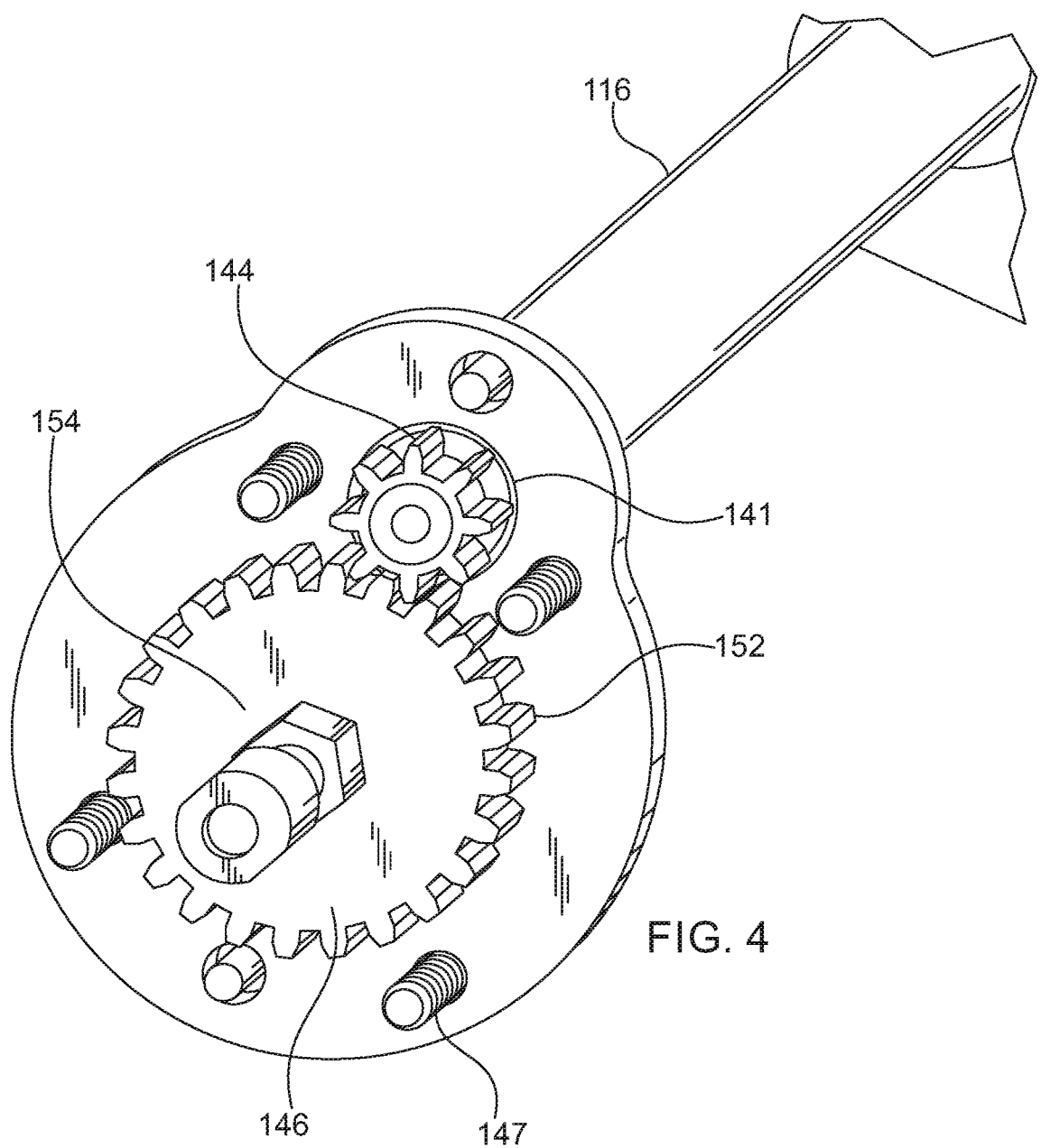
FIG. 4 is another truncated perspective view of a distal end portion of the reamer of FIG. 1, with some components removed for clarity.

A variety of housing configurations can be used to house gears in accordance with this disclosure. Referring to FIGS. 3 and 4, back plate 138 has a first, plate section 138a having a perimeter that conforms to a circle. Back plate 138 also has a second plate section 138b in the form of a lobe 148. Lobe 148 extends radially outwardly with respect to a center 139 of first plate section 138a and projects beyond the circular perimeter of the first plate section.

Back plate 138 has a proximal end 143 that attaches to sleeve 116 (shown in FIG. 1) and a distal end 145 that attaches to sidewall 142 (shown in FIG. 3). Back plate 138 further defines an aperture 141 that extends through the back plate between proximal end 143 and distal end 145 so as to provide an opening into gear box 132. Aperture 141 has a circular perimeter that is concentric with a circle conforming to the circular perimeter of lobe 148. Distal end 122 of sleeve 116 attaches to back plate 138 in coaxial alignment with aperture 141. A distal end 164 of flexible drive shaft 160 is positioned adjacent distal end 122 of sleeve 116, and therefore is also adjacent to aperture 141. Driver gear 144 is attached to distal end 164 of flexible drive shaft 160 through aperture 141. In this arrangement, flexible drive shaft 160 is operable to apply torque to driver gear 144.

Aperture 141 extends through back plate 138 along an axis perpendicular to proximal end 143 and distal end 145. This orientation accommodates a drive shaft that is connected to back plate 138 at a right angle. As noted earlier, sleeves and drive shafts according to this disclosure can attach to gear boxes at non-perpendicular angles. In such arrangements, the aperture would extend at a non-perpendicular angle with respect to the proximal end of the back plate that corresponds to the angle at which the drive shaft approaches the back plate.

Driver gear 144 has a plurality of teeth 144a, and follower gear 146 has a plurality of teeth 146a that mesh with teeth 144a. As such, follower gear 146 is configured to rotate in response to rotation of driver (leer 144. Follower gear 146 has a proximal end 152 that faces back plate 138 and a distal end 154 opposite proximal end 152. Distal end 154 of follower gear 146 is attached to an output shaft 156. Output shaft 156 projects distally from follower gear 146 and rotates in unison with the follower gear. Output shaft 156 has first section 156a configured to mate with cutting face 170. First section 156a is configured to transfer rotational force from follower gear 146 to cutting face 170 when the follower gear is rotated by driver gear 144.

Cutting faces in accordance with the present disclosure can have a variety of cutting geometries. The chosen geometry may depend on the type of reaming operation, the location of the procedure, or other factors. For example, the cutting face may be circular with a plurality of radially extending cutting edges that form a substantially flat profile. Examples of circular configurations with flat cutting profiles are described and shown in U.S. Pat. No. 9,517,076, the content of which is incorporated by reference herein in its entirety. Cutting faces in accordance with the present disclosure can also have other configurations, including a step-shaped profile or curved profile.

In the present example, cutting face 170 has a circular base 172 and a plurality cutting members 174. Cutting members 174 collectively form a dome-shaped profile that extends distally from base 172. Each cutting member 174 has a cutting edge 175. In addition, each cutting member has a first end 174a near the center of base 172 and a second end 174b adjacent the perimeter of the base. Each first end 174a extends distally from base 172 by a first distance, and each second end 174b extends distally from the base by a second distance. The first distance is greater than the second distance, such that each cutting edge 175 gradually curves toward base 172 as it progresses radially outwardly from the center of cutting face 170. Each cutting edge 175 has a convex curvature that combines with the convex curvatures of the other cutting edges to form the dome-shaped profile.

Reamer heads in accordance with this disclosure may include one or more optional components to align and stabilize the reamer head during reaming. In the present example, output shaft 156 includes a second output shaft section 156b that projects distally beyond cutting edges 175. Second output shaft section 156b is configured to maintain reamer head 130 in a correct position of alignment during reaming. To this end, second output shaft section 156b takes the form of a drill bit 158. Drill bit 158 is operable to drill into bone at the beginning of a reaming operation to fix the rotational axis of cutting face 170. Once drill bit 158 engages bone, the drill bit fixes the cutting face axis 171 of cutting face 170 so that the cutting face remains stable and cannot move laterally as it rotates during a reaming operation. This, in turn, allows the cutting edges 175 to cut a concave-shaped or cup-shaped profile into the bone.

Reamer heads in accordance with this disclosure can be constructed in a variety of ways. In the present example, back plate 138 and sidewall 142 are assembled together with a plurality of bolts 147.

Reamer heads in accordance with this disclosure can be attached to sleeves and drive shafts in a variety of ways. In the present example, second sleeve section 116b and flexible drive shaft 160 intersect back plate 138 at a right angle. As such, the cutting face axis 171 of cutting face 170 is parallel to second sleeve axis 118. As noted earlier, sleeves and drive shafts in accordance with the present disclosure can also connect to reamer heads at non-right angles, and need not necessarily be perpendicular. Different gear assemblies, including but not limited to assemblies with bevel gears, worm gears and/or other gears in the gear box, can also be used to allow sleeves and drive shafts to connect with the reaming head at various angles less than or greater than ninety degrees. For example, the driver gear and follower gear could be bevel gears, each having teeth cut at an angle of 22.5 degrees, to allow the second sleeve section and drive shaft to connect to the driver gear at an angle of 45 degrees relative to the cutting face axis. It is contemplated that interchangeable gears may also be used on the ends of drive shafts to allow drive shafts to connect to the reamer head at different angles.

Various gear assemblies can also be employed in accordance with the present disclosure, and need not consist of only two gears. For example, the gear box may house a series of three or more gears to transfer torque from a drive shaft to the cutting face. As such, the gear box may have various geometries dictated by the number, size and arrangement of gears. For example, the gear box may have a longer narrower shape as compared to the pear shaped gear box, shown in the drawings.

Accordingly, it is intended that the present disclosure covers all such variations, as well as different combinations or substitutions of features that are described herein.

What is claimed:

1. A reaming instrument comprising:
    a reamer head having a cutting face, the cutting face rotatable about a cutting face axis;
    a hollow handle section extending from a proximal end to a distal end, with the distal end connected to the reamer head; and
    a drive shaft operably connected to the cutting face at a point spaced radially outwardly from the cutting face axis;
    wherein the drive shaft extends through the hollow handle section and terminates at an engagement end located at the proximal end of the hollow handle section;
    wherein the drive shaft is a flexible drive shaft.

2. The reaming instrument of claim 1, wherein the drive shaft extends through a sleeve.

3. The reaming instrument of claim 1, further comprising a post.

4. The reaming instrument of claim 1, further comprising a handle portion.

5. The reaming instrument of claim 1, wherein the reamer head comprises a gear box.

6. The reaming instrument of claim 5, wherein the gear box comprises a driver gear and a follower gear.

7. The reaming instrument of claim 6, wherein the driver gear is operatively coupled to the drive shaft.

8. The reaming instrument of claim 6, wherein the follower gear is operatively coupled to the cutting face.

9. The reaming instrument of claim 8, wherein the follower gear is connected to an output shaft, and wherein the output shaft is connected to the cutting face.

10. The reaming instrument of claim 9, wherein the output shaft comprises a drill bit.

11. The reaming instrument of claim 1, wherein the reamer head comprises a back plate, and the drive shaft extends through a sleeve attached to the back plate.

12. The reaming instrument of claim 11, wherein the back plate extends in a plane that is orthogonal to the cutting face axis, and the sleeve and drive shaft attach to the back plate at a right angle to the plane.

13. The reaming instrument of claim 11, wherein the sleeve defines a sleeve axis.

14. The reaming instrument of claim 13, wherein the sleeve axis extends parallel to but offset from the cutting face axis.

15. The reaming instrument of claim 11, wherein the back plate comprises a first plate section having a first center and a first perimeter that conforms to a first circle extending around the first center.

16. The reaming instrument of claim 15, wherein the back plate comprises a second plate section in the form of a lobe that extends radially outwardly with respect to the first center of the first plate section.

17. The reaming instrument of claim 16, wherein the lobe defines a second perimeter conforming to a second circle that intersects the first circle.

18. The reaming instrument of claim 17, wherein the second circle extends around a second center, and the back plate defines an aperture that extends through the second center.

19. The reaming instrument of claim 18, wherein the drive shaft operably connects to the cutting face through the aperture.

20. The reaming instrument of claim 1, wherein the hollow handle section extends parallel to the cutting face axis.

21. The reaming instrument of claim 1, wherein the hollow handle section is connected to the reamer head by a sleeve, and the flexible drive shaft extends through the sleeve.

22. The reaming instrument of claim 21, wherein the sleeve extends from a proximal sleeve end at the distal end of the hollow handle section to a distal sleeve end at the reamer head, and the sleeve comprises an S-curved section joining a the proximal sleeve end to the distal sleeve end.

23. The reaming instrument of claim 22, wherein the hollow handle section extends along the cutting face axis.

24. The reaming instrument of claim 21, wherein the sleeve extends from a proximal sleeve end at the distal end of the hollow handle section to a distal sleeve end at the reamer head, and a portion of the sleeve between the proximal sleeve end and the distal sleeve end extends along a sleeve axis that is parallel to and radially spaced outwardly from the cutting face axis.

25. A reaming instrument comprising:
a reamer head having a cutting face, the cutting face rotatable about a cutting face axis; and
a drive shaft operably connected to the cutting face at a point spaced radially outwardly from the cutting face axis;
wherein the reamer head comprises a gear box having a driver gear operatively coupled to the drive shaft, and a follower gear operatively coupled to the cutting face; and
wherein the follower gear is connected to an output shaft connected to the cutting face and the output shaft comprises a drill bit.

26. A reaming instrument comprising:
a reamer head having a cutting face that is rotatable about a cutting face axis;
a hollow handle section extending from a proximal end to a distal end, with the distal end connected to the reamer head; and
a drive shaft operably connected to the cutting face at a point spaced radially outwardly from the cutting face axis, wherein the drive shaft extends through the hollow handle section and terminates at an engagement end located at the proximal end of the hollow handle section; and
a gear assembly in the reamer head, the gear assembly comprising:
a driver gear operatively coupled to the drive shaft,
a follower gear operatively connected to the driver gear,
an output shaft connected to the follower gear and to the cutting face, wherein the output shaft comprises a drill bit.

* * * * *